United States Patent

Hamminga et al.

Patent Number: 5,332,746
Date of Patent: Jul. 26, 1994

[54] 8,9-ANNELATED-$\beta$-CARBOLINES AND 8,9-ANNELATED 3,4-DIHYDRO-$\beta$-CARBOLINES

[75] Inventors: Derk Hamminga; Hans H. Haeck; Ineke van Wijngaarden; Johannes W. C. M. Jansen, all of Weesp, Netherlands

[73] Assignee: Duphar International Research B.V., Weesp, Netherlands

[21] Appl. No.: 700,058

[22] Filed: May 8, 1991

Related U.S. Application Data

[63] Continuation of Ser. No. 366,535, Jun. 15, 1989, abandoned.

[30] Foreign Application Priority Data

Jun. 20, 1988 [NL] Netherlands ............... 8801565
Jan. 20, 1989 [NL] Netherlands ............... 8900136

[51] Int. Cl.$^5$ ............... A61K 31/445; C07D 471/14
[52] U.S. Cl. ............... 514/278; 514/287; 514/288; 546/18; 546/66; 546/64
[58] Field of Search ............... 546/66, 18, 64; 514/288, 287, 278

[56] References Cited

U.S. PATENT DOCUMENTS

| | | | |
|---|---|---|---|
| 4,190,657 | 2/1980 | Koletar | 514/288 |
| 4,200,638 | 4/1980 | Hannart | 514/288 |
| 4,617,305 | 10/1986 | Hannart | 514/278 |

FOREIGN PATENT DOCUMENTS

| | | |
|---|---|---|
| 0300541 | 1/1989 | European Pat. Off. |
| 0320075 | 6/1989 | European Pat. Off. |
| 7812605 | 7/1980 | Netherlands ............... 514/288 |
| 975835 | 11/1964 | United Kingdom . |

*Primary Examiner*—Robert W. Ramsuer
*Assistant Examiner*—Jacqueline Haley
*Attorney, Agent, or Firm*—Stevens, Davis, Miller & Mosher

[57] ABSTRACT

The invention relates to a group of new 8,9-annelated-$\beta$-carbolines and 8,9-annelated-3,4-dihydro-$\beta$-carbolines having interesting fibrinolytic properties. In particular the compounds can be used as orally active fibrinolytics.

The compounds have the general formulae 1 and 2

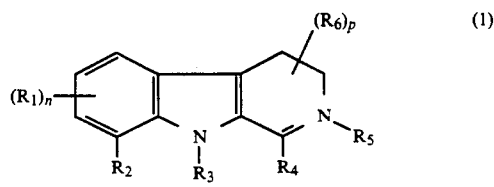

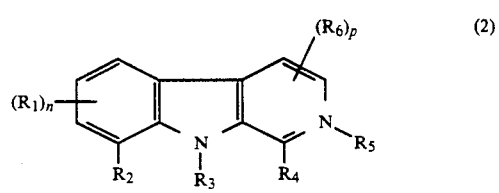

wherein $R_2 + R_3$ together with the carbon atom and the nitrogen atom to which they are bound and the intermediate carbon atom constitute a heterocyclic group consisting of 5–10 ring atoms.

6 Claims, No Drawings

8,9-ANNELATED-β-CARBOLINES AND 8,9-ANNELATED 3,4-DIHYDRO-β-CARBOLINES

This application is a continuation of application Ser. No. 366,535, filed Jun. 15, 1989 now abandoned.

The invention relates to new 8,9-annelated-β-carboline derivatives and 8,9-annelated-3,4-dihydro-β-carboline derivatives and salts and prodrugs thereof, to the preparation of the said compounds and pharmaceutical compositions which comprise at least one of these compounds as an active substance. It has been found surprisingly that compounds of formulae 1 and 2

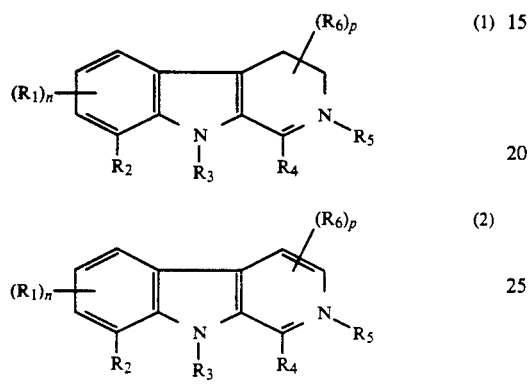

and the salts and prodrugs thereof have good fibrinolytic properties and in particular may be used as orally active fibrinolytics.

The symbols in the above formulae 1 and 2 have the following meanings:

$R_1$ independently of each other are straight or branched alkyl having 1-4 C-atoms, fluorinated or hydroxylated alkyl having 1-4 C-atoms, or two alkyl groups $R_1$ bonded to adjacent carbon atoms together constitute a ring of 5-7 carbon atoms, or $R_1$ is cycloalkyl having 3-6 C-atoms, or $R_1$ is straight or branched alkoxy, alkylthio or alkylsulphonyl having 1-4 C-atoms which may be substituted with one or more fluorine atoms or with one optionally substituted phenyl group, or two alkoxy groups and/or alkylthio groups bonded to adjacent carbon atoms may form a ring consisting of 5 or 6 ring atoms, or $R_1$ is a cycloalkoxy group or a cycloalkylthio group having 3-6 C-atoms, or $R_1$ is straight or branched alkoxy-, alkylthio- or alkylsuphonylalkyl having 2-6 C-atoms, or $R_1$ is hydroxy, halogen, cyano, straight or branched alkoxycarbonyl having 1-4 C-atoms in the alkoxy group;

n has the value 0-2;

$R_2 + R_3$ together with the carbon atom and the nitrogen atom to which they are bound and the intermediate carbon atom constitute a heterocyclic group which consists of 5-10 ring atoms and which, in addition to the nitrogen atom already present, may comprise a second hetero atom from the group O, S, S—O or $SO_2$, and which may be substituted with alkyl groups which can form a spiroalkyl group, or the ring formed by $R_2 + R_3$ may be annelated with a saturated or unsaturated carbocyclic or heterocyclic ring which consists or 5- or 6-ring atoms and which may optionally be substituted;

$R_4$ is hydrogen, straight or branched alkyl having 1-8 C-atoms, alkoxy- or alkylthioalkyl, alkenyl or alkynyl, which groups may be subsituted with one or more fluorine atoms, or with a cycloalkyl group, or with a phenyl group which may be substituted with one or two substituents, which optionally form a ring which is annelated with the phenyl group, or $R_4$ is cycloalkyl having 3-8 C-atoms or cycloalkenyl having 5-7 C-atoms which rings may be substituted with methyl groups, or $R_4$ is a bridged hydrocarbon group, or $R_4$ is straight or branched alkoxycarbonylalkyl having 1-6 C-atoms in the alkoxy group and 1-3 C-atoms in the alkyl group, or $R_4$ is a group $R_7R_8N—CO—R_9—$ or $R_7R_8N—SO_2—R_9$, wherein $R_7$ and $R_8$ independently of each other are hydrogen, alkyl having 1-3 C-atoms, or together with the nitrogen atom to which they are bound constitute a heterocyclic 5- or 6-ring, and $R_9$ is alkyl having 1-3 C-atoms, or $R_4$ is alkylsulphonylalkyl having 1-3 C-atoms per alkyl group, or a phenylsulphonylalkyl group having 1-3 C-atoms in the alkyl group and of which the phenyl group may be substituted, or $R_4$ is a phenyl group substituted with 0-3 groups $R_{10}$, wherein $R_{10}$ independently of each other are straight or branched alkyl having 1-6 C-atoms which may be substituted with one or more fluorine atoms, or with one cyano group, or with straight or branched alkoxycarbonyl having 1-6 C-atoms in the alkoxy group, or with a group $R_7R_8N—CO—$ or $R_7R_8N—SO_2—$, wherein $R_7$ and $R_8$ have the above-mentioned meanings, or two groups $R_{10}$ bonded to adjacent carbon atoms form a carbocyclic ring which consists of 5-7 ring atoms and is annelated with the phenyl group, or $R_{10}$ is straight or branched alkyl(1-4 C)-oxy-alkyl(-0-3 C) or alkyl(1-4 C)-thioalkyl(0-3C), which groups may comprise one or more fluorine atoms, or of which two alkoxy groups or alkylthio groups bonded to adjacent carbon atoms form a ring consisting of 5-7 ring atoms, or $R_{10}$ is cycloalkoxy, cycloalkylthio or cycloalkylsuphonyl having 3-6 C-atoms, or $R_{10}$ is cycloalkyl having 3-6 C-atoms, or $R_{10}$ is straight or branchedalkoxycarbonyl, a group $R_7R_8N—CO—$ or $R_7R_8N—SO_2—$ wherein $R_7$ and $R_8$ have the above-mentioned meanings, or $R_{10}$ is halogen or hydroxy, or $R_4$ is a mono- or bicyclic heteroaryl group in which N and/or O and/or S may be present as hetero atoms; $R_5$ is absent or $R_5$ is alkyl (with an anion as counter ion), or oxygen;

p has the value 1 or 2; and $R_6$ indepently of each other are hydrogen, on the understanding that at least one group $R_6$ is alkyl having 1-6 C-atoms, a halogen atom, a nitrile group, an amino group, an acylamino group, an alkoxycarbonylamino group, a group —NH—CO—$NR_7R_8$, wherein $R_7$ and $R_8$ have the above-mentioned meanings, a straight or branched alkoxycarbonyl group having 1-8 C-atoms in the alkoxy group, (0-3 C)alkoxy-(1-2 C)-alkoxycarbonyl, a benzyloxycarbonyl group optionally substituted in the benzene ring, a group $R_7R_8N—SO_2—$ or $R_7R_8N—CO—$, wherein $R_7$ and $R_8$ have the above-mentioned meanings, or $R_6$ is hydroxymethyl, esterified hydroxymethyl, alkoxymethyl having 1-6 C-atoms in the alkoxy group, a benzyloxymethyl group optionally substituted in the benzene ring, or an alkyl(1-6 C)-$SO_2$-group.

Suitable acids with which the compounds of formulae 1 and 2 according to the invention can form pharmaceutically acceptable acid addition salts are, for example, hydrochloric acid, suphuric acid, phosphoric acid, nitric acid, and organic acids, for example, citric acid, fumaric acid, maleic acid, tartaric acid, acetic acid, benzoic acid, p-toluene sulphonic acid, methane sulphonic acid, and the like.

The compounds of formulae 1 and 2 may comprise one or more chiral centres. The invention relates both to racemates and to individual enantiomers.

The invention also relates to prodrugs of the compounds of formulae 1 and 2, i.e. derivatives of these compounds which as such are inactive, from which an active compound of formulae 1 and 2 is formed after splitting off an easily removable group, for example, an ester group or an ether group.

The carboline derivatives according to the invention are orally active fibrinolytics and may hence be used in controlling already formed venous or arterial thrombi, or may be administered to prevent thrombi. The compounds may be used, for example, for a short period of time in operations or for a long period of time in enhanced risk after, for example, myocardial infarct, cerebral or periferal suffering. The best compounds possibly operate via an increase of the tissue plasminogen activator activity, as a result of which the possibility of spontaneous bleedings can be prevented.

The oral fibrinolytic activity of the compounds according to the invention was established in the first instance in rats in the so-called DBCLT (diluted blood clot lysis test; Taylor F. B. et al, Fed. Proc. (1981), 40, 2092-2098). Rats are treated orally with the compound to be tested. After 1-3 hours blood is taken. $^{125}$I-labelled fibrinogen and thrombine are added as a result of which a blood clot is formed which, depending on the extent of fibrinolytic activity caused by the compound to be tested, dissolves more rapidly as compared with blood clots of untreated animals.

The increase of tissue plasminogen activator activity was measured in cultures of endothelium cells (Thrombosis Diathesis Haemorrhagis (Stuttgart), 34, (1975), pp. 825-839; and Thrombosis and Haemostasis, 51, (1984), p. 392).

The pharmacologically active compounds belonging to the invention, their salts and prodrugs can be brought into forms suitable for administration, for example, pills, tablets, coated tablets, capsules, powders, injection liquids, and the like, by means of techniques conventionally used for this purpose, and while using suitable auxiliary substances, for example, solid or liquid carrier materials.

The dosage in which the compounds according to the invention may be used depend on the severity and the nature of the disease to be treated and on the mode of administration.

The compounds of formula 1, wherein $R_1$-$R_6$, n and p have the above mentioned meanings can be prepared in at least one of the following manners. For example, the compounds of formula 1, wherein the substituent $R_5$ is not present, can be prepared a) by a Bischler-Napieralski ring closure of a compound of formula 3

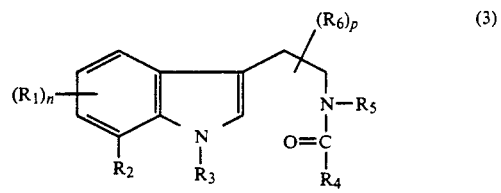

wherein $R_1$-$R_4$, $R_6$, n and p have the meanings mentioned in formula 1 and $R_5$ is hydrogen. Suitable methods for Bischler-Napieralski ring closures are described inter alia in Organic Reactions vol. VI., p. 174.

The starting compounds of formula 3 required for this mode of preparation can be obtained in a manner known per se, for example, by reaction of a compound of formula 4

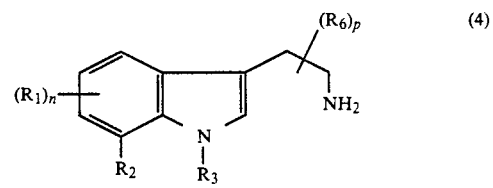

wherein $R_1$, $R_2$, $R_3$, $R_6$, n and p have the meanings mentioned in formula 1, with a compound of formula $R_4$—CO—Y, wherein $R_4$ has the above-mentioned meaning and Y is a reactive group, for example, halogen, ethoxycarbonyloxy, etc.

The required starting compounds of formula 4 can be obtained in a manner known per se by reaction of a compound of formula 5

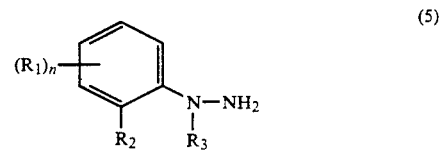

with a compound of formula 6

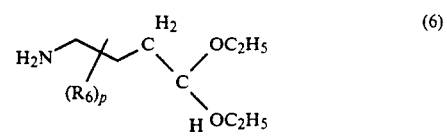

or with a compound of formula 7

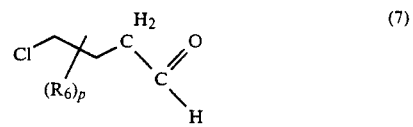

The starting compounds of formula 4 which have the structure of formula 8

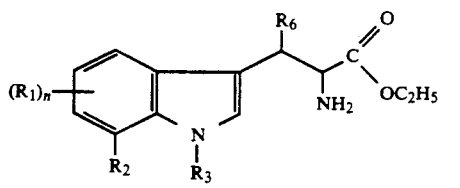
(8)

wherein $R_1$, $R_2$, $R_3$, $R_6$, and n have the meanings mentioned in formula 4 can be obtained in a good yield in particular by reaction of the analogous compounds of formula 5 with a compound of formula 9

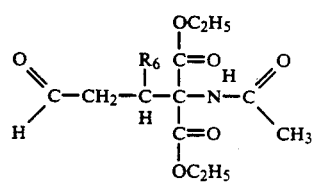
(9)

The compound of formula 10 thus obtained

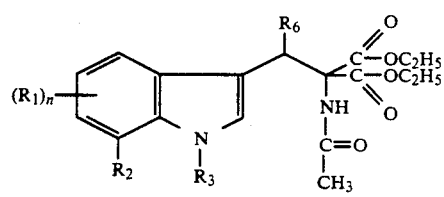
(10)

may be converted according to methods known per se into the analogous compounds of formula 8 by hydrolysis and decarboxylation succeeded by an esterification of the carboxylic acid analoga of the compounds of formula 8 thus obtained.

b) by dehydrogenation of a compound of formula 11 or a salt thereof

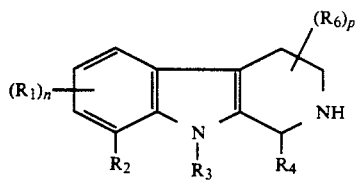
(11)

wherein $R_1$, n, $R_2$, $R_3$, $R_4$, $R_6$, and p have the meanings mentioned in formula 1 with a suitable oxidant. In particular the compounds of formula 1 can be prepared in a good yield by dehydrogenation with potassium permanganate, for example, as described in Synthesis, Synthetic Communications (1985), pp. 1134-1135. The reaction is preferable carried out in a suitable solvent, for example, tetrahydrofuran, dioxan, etc., at temperatures from −10° to 20° C., in an atmosphere of nitrogen. The starting compounds required for this mode of preparation of formula 11 can be obtained in a manner analogous to the method described in Advances in Heterocyclic Chemistry, vol. 3, pp. 79-207 (The Carbolines). More particularly, compounds of this type can be obtained in a good yield by reaction of a compound of formula 4 or salt thereof, wherein $R_1$, n, $R_2$, $R_3$, $R_6$, and p have the above-mentioned meanings, with an aldehyde of formula 12

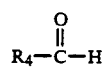
(12)

wherein $R_4$ has the above-mentioned meaning. The reaction is preferably carried out in a suitable solvent, for example, acetic acid, alcohol, etc., at a temperature between 10° and 120° C.

The compounds of formula 2, wherein $R_1$, n, $R_2$, $R_3$, $R_4$, $R_5$, $R_6$ and p have the meanings mentioned in formula 2 can be prepared in at least one of the following manners.

Compounds of formula 2 in which the substituent $R_5$ is absent can be obtained from a compound of formula 1 or 11, wherein $R_1$, n, $R_2$, $R_3$, $R_4$, $R_6$ and p have the meanings mentioned in formula 1 or 11 1) by dehydrogenating this compound in the presence of a suitable catalyst, for example, palladium on carbon, preferably in a suitable solvent, for example, xylene, at temperatures from 80°-220° C., or 2) by conversion with sulphur, preferably in a suitable solvent, for example, xylene, at temperatures from 80°-220° C., or 3) by dehydrogenation with a suitable oxidant, for example potassium permanganate preferably in a suitable solvent, for example tetrahydrofuran or dioxan, at temperatures between −10° and 100° C., or 4) by reaction of a compound of formula 2, wherein $R_1$, n, $R_2+R_3$, $R_4$, $R_5$ and p have the meanings mentioned in formula 2 and one group $R_6$ is a group —CO—Y—, wherein Y is a hydroxy group, a halogen atom or a reactive group, for example, the group $C_2H_5O$—CO—O— or the group of formula 13

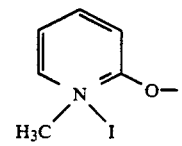
(13)

with a compound or the formula A-X, wherein X is a hydrogen atom or an alkalimetal atom, and A is (1-8 C)-alkyl-O—, (1-3)alkoxy-(1-2 C)alkyl-O, benzyl-O optionally substituted in the benzene ring, $R_7R_8$—N—, wherein $R_7$ and $R_8$ have the above-mentioned meanings, or 5) by withdrawing water from a compound of formula 14

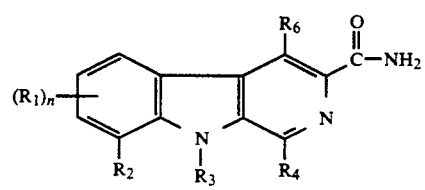
(14)

or 6) by reaction of a compound of formula 15

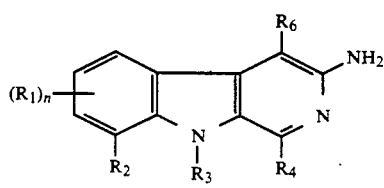
(15)

with a compound Cl—CO—Q or O=C=N—L, wherein Q is alkyl, alkoxy or a group $R_7R_8N$—, and L is alkyl or 7) by reduction of a compound of formula 2, wherein $R_1$, n, $R_2+R_3$, $R_4$, $R_5$, and p have the meanings mentioned in formula 2 and wherein $R_6$ is an alkoxycarbonyl group, with a suitable reducing agent, for example, lithium aluminium hydride.

The compounds of formulae 1 and 2, wherein $R_5$ is oxygen and wherein the remaining symbols have the meaning mentioned in formulae 1 and 2, can be prepared, for example, by oxidation of the analogous compounds of formulae 1 and 2, wherein $R_5$ is absent, with a suitable oxidant, for example, perbenzoic acid, peracetic acid, hydrogen peroxide, etc., preferably in a suitable solvent, for example, chloroform, acetic acid or water at temperatures from 0°–100° C.

The invention will now be described in greater detail with reference to the ensuing specific examples.

EXAMPLE I 10-ethoxycarbonyl-8-phenyl-11-methyl-5,6-dihydro-4H-pyrido[4',3':4,5]pyrrolo[3,2,1-ij]quinoline hydrochloride a)

1-[2-acetylamino-2,2-di-(ethoxycarbonyl)-1-methylethyl]-5,6-dihydro-4H-pyrrolo[3,2,1-ij]quinoline 0.11 g of sodium was brought in 63 ml of absolute alcohol. 14.8 g (0.068 mol) of acetylamino-diethylmalonate were added to the reaction mixture. 5.2 ml (0.074 mol) of crotonaldehyde were then added dropwise while stirring at 3°–7° C., after which stirring was continued for 3 hours without cooling. 1.9 ml of acetic acid and 10.0 g (0.068 mol) of 1-amino-tetrahydroquinoline were then added and boiled while stirring for 90 minutes. Evaporation was then carried out. The residue was taken up in methylene chloride and washed with water. The methylene chloride solution was evaporated and the residue was chromatographed over silicagel using methylene chloride/methanol 99:1 as an eluent. By evaporating the desired fraction 18.4 g (65%) of the hydrazone was obtained.

18.3 g (0.044 mol) of the resulting hydrazone were heated to boiling while stirring vigorously in a mixture of 84 ml water and 4.2 ml of concentrated sulphuric acid. After boiling for 2 hours the mixture was cooled and shaken with methylene chloride. The methylene chloride solution was separated, washed with water and evaporated in vacuum. The residue was chromatographed over silicagel using methylene chloride/methanol (98/2) as an eluent. By evaporating the desired fraction 13.7 g (78%) of the desired product were obtained b)

2-amino-3-(5,6-dihydro-4H-pyrrolo[3.2.1-ij]quinolin-1-yl)-3-methyl-propanoic acid ethyl ester 8.2 g (20.5 mmol) of the final product of a) were added to a solution of 4.2 g of sodium hydroxide in 42 ml of water. The mixture was boiled for 2.5 hours, cooled and acidified with 75 ml of 2N hydrochloric acid. The precipitate was sucked off and dried. In this manner 6.2 g (87%) of the dicarboxylic acid were obtained.

6.1 g (18 mmol) of the above dicarboxylic acid were added to a mixture of 50 ml of water and 8.5 ml of alcohol. A solution of 4.4 g of sodium hydroxide in 4.5 ml of water was then added and the mixture was boiled for 72 hours. The reaction mixture was then cooled and acidified with 6.6 ml of acetic acid and extracted with methylene chloride. The methylene chloride solution was dried and evaporated in vacuum. Yield 3.3 g (72%) of crude product which was sufficiently pure for further reactions.

1.15 g (4.5 mmol) of the resulting product were added to the reaction mixture of 2.2 mol of acetylchloride and 7 ml of alcohol. The mixture was boiled for 2.5 hours and evaporated in vacuum. The residue was then shaken with methylene chloride and a soda solution. The methylene chloride layer was separated, dried and evaporated. The residue was chromatographed over silicagel using methylene chloride/methanol (9/1) as an eluent. By evaporating the desired fractions, 0.87 g (69%) of the desired amino acid ethyl ester were obtained.

c)

10-ethoxycarbonyl-8-phenyl-11-methyl-5,6,8,9,10,11-hexahydro-4H-pyrido-[4',3':4,5]pyrrolo[3,2.1ij]quinoline 0.85 g (3 mmol) of the final product of b) were dissolved in acetic acid. 0.35 g (3.3 mmol) of benzaldehyde were added and the mixture was stirred at 50° C. for 20 hours. The reaction mixture was made basic with a potassium carbonate solution and shaken with methylene chloride. The methylene chloride layer was separated and evaporated. The residue was chromatographed over silicagel using ether/petroleum ether (1/1) as an eluent. By evaporating the desired fractions, 0.6 g (55%) of the desired product (mixture of isomers) were obtained.

d)

10-ethoxycarbonyl-8-phenyl-11-methyl-5,6-dihydro-4H-pyrido[4',3':4,5]pyrrolo[3,2,1-ij]quinoline hydrochloride 0.6 g (1.6 mmol) of the above product were dissolved in 35 mol of tetrahydrofuran and cooled to 0° C. 3.2 g of potassium permanganate powder were then added slowly, after which stirring at room temperature was carried out for 72 hours, The mixture was then filtered over hyflo. The filtrate was evaporated and the residue was chromatographed over silicagel using ether/petroleum ether (1/1) as an eluent. The desired fractions were evaporated and the residue was dissolved in alcoholic hydrochloric acid and again evaporated in vacuum. 0.2 g (31%) of the desired hydrochloride were obtained having a melting-point of 160°–164° C.

EXAMPLE II 10-ethoxycarbonyl-8-phenyl-5,6-dihydro-4H-pyrido[4',3':4,5]pyrrolo[3,2,1-ij]quinoline 3.6 g (10 mmol) of 10-ethoxycarbonyl-8-phenyl-5,6,8,9,10,11-hexahydro-4H-pyrido[4',3':4,5]pyrrolo[3,2,1-ij]quinoline (a mixture of isomers), obtained analogously to the method of example I a) to c) were boiled while stirring for 8 hours together with 0.8 g (25 mmol) of sulphur in 25 ml of xylene. Another 0.2 g of sulphur were added and boiling with stirring was carried out for another 8 hours. The reaction mixture was evaporated in vacuum and chromatographed over 150 g of silicagel using methylene chloride with 10% by volume of ethyl acetate as an eluent. The desired fraction was evaporated in vacuum. The residue was crystallised from 10 ml of ethyl acetate. 2.1 g (59%) of the desired product were obtained having a melting-point of 173°-174° C,

EXAMPLE III 8-cyclohexyl-5,6-dihydro-10-ethoxycarbonyl-4H-pyrido-[4',3':5]pyrrolo[3,2,1-ij]quinoline hydrochloride 5.3 g (14.4 mmol) of 8-cyclohexyl-10-ethoxycarbonyl-5,6,8,9,10,11-hexahydro-4H-pyrido[4',3':4,5]pyrrolo-[3,2,1-ij]quinoline obtained according to the method of example I a) to c) were dissolved in 250 ml of xylene. Palladium on carbon 10% was added and stirred for 24 hours while boiling. Filtration over hyflo was then carried out. The filtrate was evaporated and the residue was chromatographed over silicagel using methylene chloride as an eluent. The desired fractions were evaporated and the residue was dissolved in ethyl acetate. After the addition of alcoholic hydrochloric acid and sucking off the solid, 3.3 g (57%) of the desired product were obtained having a melting-point of 172°-174° C.

In an analogous manner were prepared;

According to example I:

(1) 10-ethoxycarbonyl-8-trifluoromethyl-5,6-dihydro-4H-pyrido[4',3':4,5]pyrrolo[3,2,1-ij]quinoline; yield: 44%, melting-point 135°-137° C.;

(2) 12-ethoxycarbonyl-10-(4-methylphenyl)-5,6,7,8-tetrahydro-4H-pyrido[4',3':4,5]pyrrolo[3,2,1-kl] [1]-benzazocin hydrochloride; yield: 48%, melting-point 168°-169° C.;

According to example II:

(3) 10-ethoxycarbonyl-8-(4-methylphenyl)-5,6-dihydro-4H-pyrido[4',3':4,5]pyrrolo[3,2,1-ij]quinoline; yield: 25%, melting-point 178°-179° C.;

(4) 10-ethoxycarbonyl-8-(4-methoxyphenyl)-5,6-dihydro-4H-pyrido[4',3':4,5]pyrrolo[3,2,1-ij]quinoline; yield: 30%, melting-point 184°-185° C.;

According to example III:

(5) 8-ethoxycarbonyl-10-phenyl-1,2-dihydro-pyrido[4',3':4,5]pyrrolo[1,2,3,-de][1,4]benzothiazine hydrochloride; yield: 41%, melting-point 242°-243° C.

(6) 11-ethoxycarbonyl-9-(4-methylphenyl)-4,5,6,7-tetrahydro-pyrido[4',3':4,5]pyrrolo[3,2,1-jk]-[1]-benzazepine; yield 52%; melting-point 182°-183° C.

EXAMPLE IV a)

10-butoxycarbonyl-8-phenyl-5,6-dihydro-4H-pyrido-[4',3':4,5]pyrrolo[3,2,1-ij]-quinoline 2.3 g (6.5 mmol) of 10-ethoxycarbonyl-8-phenyl-5,6 dihydro-4H-pyrido[4',3':4,5]pyrrolo[3,2,1-ij]quinoline were dissolved in 60 ml of 90% alcohol. 1.1 Equivalent of 2N sodium hydroxide solution were added and the mixture was boiled for 45 minutes. Neutralisation with 2N hydrochloric acid was then carried out. The solid was sucked off and dried. Yield: 1.6 g (74%) of the carboxylic acid having a melting-point of 275° C. (decomp.).

1.4 g (4.2 mmol) of this acid were suspended in 30 ml of methylene chloride. 6 ml of thionylchloride were added and the mixture was boiled for 1 hour. The reaction mixture was evaporated in vacuum and a mixture of 40 ml of butanol and 3 ml of triethylamine was added to the residue, after which the mixture was evaporated. The residue was dissolved in methylene chloride and the methylene chloride solution was washed with water and evaporated. The residue was chromatographed over siliagel using methylene chloride/methanol (98/2) as an eluent. After evaporating the desired fractions, 1.7 g (68%) of the desired product having a melting-point of 145°-146° C. were obtained.

In an analogous manner were obtained:

(1) 10-benzyloxycarbonyl-8-phenyl-5,6-dihydro-4H-pyrido[4',3':4,5]pyrrolo[3,2,1-ij]quinoline hydrochloride; yield: 32%, melting-point: 150°-152° C.;

(2) 10-isopropoxycarbonyl-8-phenyl-5,6-dihydro-4H-pyrido[4',3':4,5]pyrrolo[3,2,1-ij]quinoline; yield; 65%, melting-point 181°-182° C.;

EXAMPLE V

10-Cyano-8-(4-methylphenyl)-5,6-dihydro-4H-pyrido[4',3':4,5]pyrrolo[3,2,1-ij]quinoline 1,2 g (3.48 mmol) of 8-(4-methylphenyl)-5,6-dihydro-4H-pyrido[3',4':4,5]pyrrolo[3,2,1-ij]quinolinyl-10-carboxylic acid was dissolved in 60 ml of pyridine and cooled to 0° C. 0.4 g (3.49 mmol) of methane suphonyl chloride were added and the mixture was stirred for 1 hour at 0° C. Thereafter ammonia was led into the mixture for 2 minutes at 0° C., and the excess of ammonia was evaporated in vacuum at room temperature. The mixture was then cooled to 0° C. 3.4 g (29.6 mmol) of methane sulphonyl chloride were then added, and the mixture was stirred for 18 hours at room temperature. The mixture was poured into 2N hydrochloric acid and shaken with methylene chloride. The methylene chloride layer was washed with water and evaporated. The residue was chromatographed over silicagel using methylene chloride/methanol (99/1) as an eluent. In this manner 0.53 g (47%) of the desired product was obtained having a melting point of 217°-217.5° C.

EXAMPLE VI

10-Acetamido-8-(4-methylphenyl)-5,6-dihydro-4H-pyrido[4',3':4.5]pyrrolo[3,2,1-ij]quinoline a)

10-amino-8-(4-methylphenyl)-5,6-dihydro-4H-pyrido[4',3':4.5]pyrrolo[3,2,1-ij]quinoline 10 g (27 mmol) of 10-ethoxycarbonyl-8-(4-methylphenyl)-5,6-dihydro-4H-pyrido[4',3':4,5]pyrrolo[3,2,1-ij]quinoline were dissolved in a mixture of 96 ml of alcohol and 48 ml of hydrazine hydrate and the mixture was boiled for 6 hours. The reaction mixture was then evaporated to a small volume and cooled. The solid was sucked off, washed with alcohol and dried. In this manner 5.8 g (60%) of the desired carbohydrazide, having a melting point of 263°-264° C., were obtained.

1.8 g (5.1 mmol) of the obtained product were suspended in 36 ml of water, and dissolved by the dropwise addition of 0.9 ml of concentrated hydrochloric acid. A solution of 0.36 g (5.2 mmol) of sodium nitrite in 2 ml of water was then added dropwise at 0° C. The reaction mixture was made alkaline with sodium bicarbonate. The precipitate was sucked off, washed with water and dried. Yield 1.8 g (96%); melting point 160°-162° C.

The so-obtained carboxylic acid azide was brought into a mixture of 25 ml of water and 25 ml of acetic acid and boiled for 30 minutes. The reaction mixture was then evaporated in vacuum, the residue was shaken with a mixture of bicarbonate in water and methylene chloride. The methylene chloride layer was separated, the solvent was removed by distillation, and the residue was chromatographed over silicagel using methylene chloride/methanol (97/3) as an eluent. 1.0 g (62%) of the desired amine having melting point of 224°–225° C. was obtained.

b) 10-acetamido-8-(4-methylphenyl)-5,6-dihydro-4H-pyrido[4',3':4,5]pyrrolo[3,2,1ij]quinoline 0.5 g (1.6 mmol) of the product obtained under a) were dissolved in 15 ml of methylene chloride. 0.18 g (1.76 mmol) of triethylamine) were added, and 0.13 ml (1.92 mmol) of acetyl chloride were added dropwise at room temperature. After starting for 30 minutes the mixture was shaken with a 5% solution of sodium bicarbonate. Methylene chloride was removed by evaporation in vacuum and the residue was chromatographed over silicagel using methylene chloride/methanol (98/2) as an eluent. 0.37 g (65%) of the desired product having a melting point of 214°–215° C. were obtained.

In an analogous manner the following compounds have been prepared:

1) 10-ethoxycarbonylamido-8-(4-methylphenyI)-5,6-dihydro-4H-pyrido[4',3':4,5]pyrrolo[3,2,1-ij]quinoline; Yield 44%, melting point 156°–157° C.

2) N-propyl-N'-{8-(4-methylphenyl)-5,6-dihydro-4H-pyrido[4',3':4,5]pyrrolo[3,2,1-ij]quinolinyl-10}-urea (prepared by reacting the end product of Example VIa) with propyl isocyanate); Yield 63%; melting point 262° C. (decomposition).

EXAMPLE VII 8-phenyl-10-hydroxymethyl-5,6-dihydro-4H-pyrido[4',3':4,5]pyrrolo[3,2,1-ij]quinoline 1.4 g (4 mmol) of 8-phenyl-10-ethoxycarbonyl-5,6-dihydro-4H-pyrido[4',3':4,5]pyrrolo[3,2,1-ij]quinoline were dissolved in 25 ml of tetrahydrofuran and added dropwise to a mixture of 0.5 g (13 mmol) of lithium aluminium hydride and 10 ml of ether at a temperature of 30° C. After cooling, 1 ml of water and 1 ml of 2N sodium hydroxide solution were added dropwise successively. After boiling for 15 minutes the solid was filtered off. The filtrate was evaporated in vacuum. The residue was boiled with 20 ml of ethanol and kept at 0° C. for 24 hours. The solid was sucked off and dried. Obtained were 0.95 g of the desired product having a melting-point of 209°–211° C.

EXAMPLE III 4,4-dimethyl-10-ethoxycarbonyl-8-phenyl-5,6,10,11-tetrahydro-4H-pyrido[4',3':4,5]pyrrolo[3,2.1-ij]quinoline hydrochloride 2.4 g (5.9 mmol) of 1-{2-(N-benzoyl-amino)-2!-(ethoxycarbonyl)-ethyl)-6,6-dimethyl-5,6-dihydro-4H-pyrrolo[3,2,1-ij]-quinoline were boiled in 8 ml of phosphorus oxychloride for 90 minutes. The mixture was then evaporated in vacuum and the residue was shaken with a mixture of 2N sodium hydroxide solution and with methylene chloride. The methylene chloride layer was washed with water and evaporated in vacuum. The residue was chromatographed over silicagel using methylene chloride/methanol (99/1) as an eluent. The desired fractions were evaporated in vacuum and the residue was dissolved in ethyl acetate and alcoholic hydrochloric acid was then added. The solid was sucked off and dried. 1.0 g of the desired hydrochloride was obtained having a melting-point of 176°–176.5° C.

We claim:
1. A compound of formula 1 or 2

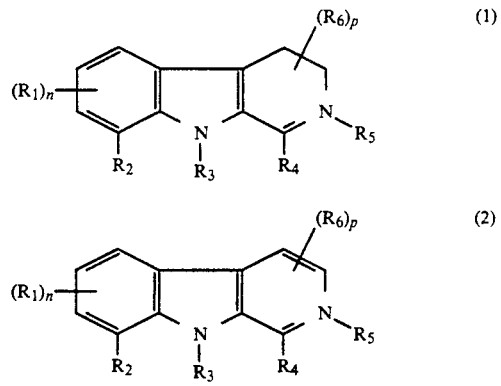

wherein the symbols have the following meanings:

$R_1$ independently of each other are straight or branched alkyl having 1–4 C-atoms, fluorinated or hydroxylated alkyl having 1–4 C-atoms, or $R_1$ is cycloalkyl having 3–6 C-atoms, or $R_1$ is straight or branched alkoxy, alkylthio or alkylsulphonyl having 1–4 C-atoms which may be substituted with one or more fluorine atoms or with one phenyl group, or $R_1$ is a cycloalkoxy group or a cycloalkylthio group having 3–6 C-atoms, or $R_1$ is straight or branched alkoxy-, alkylthio- or alkylsulphonylalkyl having 2–6 C-atoms, or $R_1$ is hydroxy, halogen, cyano, straight or branched alkoxycarbonyl having 1–4 C-atoms in the alkoxy group;

n has the value 0–2;

$R_2 + R_3$ together with the carbon atoms and the nitrogen atoms to which they are bound and the intermediate carbon atoms constitute a piperidine ring which may be substituted with alkyl groups which can form a spiroalkyl group;

$R_4$ is hydrogen, straight or branched alkyl having 1–8 C-atoms, alkoxy- or alkylthioalkyl, alkenyl or alkynyl, which groups may be substituted with one or more fluorine atoms, or with a cycloalkyl group, or with a phenyl group which may be substituted with one or two substituents selected from the group consisting of lower alkyl and lower alkoxy, or $R_4$ is a cycloalkyl having 3–8 C-atoms, or cycloalkenyl having 5–7 C-atoms which rings may be substituted with methyl groups, or $R_4$ is a straight or branched alkoxycarbonylalkyl having 1–6 C-atoms, or $R_4$ is a group $R_7R_8N-CO-R_9-$ or $R_7R_8N-SO_2-R_9-$, wherein $R_7$ and $R_8$ independently of each other are hydrogen, alkyl having 1–3 C-atoms, and $R_9$ is alkyl having 1–3 C-atoms, or $R_4$ is alkylsulphonylalkyl having 1–3 C-atoms per alkyl group, or a phenylsulphonylalkyl group having 1–3 C-atoms in the alkyl group or $R_4$ is a phenyl group substituted with 0–3 groups $R_{10}$, wherein $R_{10}$ independently of each other are straight or branched alkyl having 1–6 C-atoms which may be substituted with one or more fluorine atoms, or with one cyano group, or with straight or branched alkoxycarbonyl having 1–6 C-atoms in the alkoxy group, or with a group $R_7R_8N-CO-$ or $R_7R_8N-SO_213$, wherein $R_7$ and $R_8$ have the above-mentioned meanings, or two groups $R_{10}$ bonded to adjacent carbon atoms form a carbocyclic ring which consists of 5–7 ring atoms and is annelated with the phenyl groups, or $R_{10}$ is straight or branched alkyl(1–4 C)-oxy-alkyl(-

0-3 C) or alkyl (1-4 C)-thioalkyl(0-3 C), which groups may comprise one or more fluorine atoms, or $R_{10}$ is cycloalkoxy, cycloalylthio or cycloalkylsulphonyl having 3-6 C-atoms, or $R_{10}$ is cycloalkyl having 3-6 C-atoms, or $R_{10}$ is straight or branched alkoxycarbonyl, a group $R_7R_8N$—CO— or $R_7R_8N$—$SO_2$— wherein $R_7$ and $R_8$ have the above-mentioned meanings, or $R_{10}$ is halogen or hydroxy;

$R_5$ is absent or $R_5$ is alkyl (with an anion as counter ion), or oxygen;

p has a value 1 or 2; and $R_6$ independently or each other are hydrogen, on the understanding that at least one group $R_6$ is alkyl having 1-6 C-atoms, a halogen atom, a nitrile group, an amino group, an acylamino group, an alkoxycarbonylamino group, a group —NH—CO—$NR_7R_8$, wherein $R_7$ and $R_8$ have the above-mentioned meanings, a straight or branched alkoxycarbonyl group having 1-8 C-atoms in the alkoxy group, hydroxy-(1-2 C) alkoxycarbonyl, (1,3 C) alkoxy-(1,2 C)alkoxycarbonyl, a benzyloxycarbonyl group, a group $R_7R_8N$—$SO_2$— or $R_7R_8N$—CO—, wherein $R_7$ and $R_8$ have the above-mentioned meanings, or $R_6$ is hydroxymethyl, esterified hydroxymethyl, alkoxymethyl having 1-6 C-atoms in the alkoxy group, a benzyloxymethyl group, or an alkyl (1-6 C)—$SO_2$— group, or a pharmaceutically suitable salt thereof.

2. A compound as defined in claim 1 which is 10-ethoxycarbonyl-8-phenyl-11-methyl-5,6-dihydro-4H-pyrido[4',3':4,5]pyrrolo[3,2,1-ij]quinoline, or a pharmacologically acceptable salt thereof.

3. A compound as defined in claim 2, wherein the pharmacologically acceptable salt is the hydrochloride.

4. A compound as defined in claim 1 which is 10-ethoxycarbonyl-8-phenyl-11-methyl-5,6-dihydro-4H-pyrido[4',3':4,5]pyrrolo[3,2,1-ij]quinoline.

5. A pharmaceutical composition having fibrinolytic activity which comprise a therapeutically effective amount of a compound as claimed in claim 1 as an active substance as well as a pharmaceutically acceptable carrier.

6. A method of dissolving or preventing blood clots, characterised in that a composition as claimed in claim 5 is used.

* * * * *